US00PP18501P2

(12) United States Plant Patent
Kobayashi

(10) Patent No.: US PP18,501 P2
(45) Date of Patent: Feb. 19, 2008

(54) ***ACER PALMATUM* PLANT NAMED 'RYUSEN'**

(50) Latin Name: *Acer palmatum*
Varietal Denomination: Ryusen

(75) Inventor: Kazuhara Kobayashi, Kawaguchi (JP)

(73) Assignee: ItSaul Plants, LLC, Atlanta, GA (US)

( * ) Notice: Subject to any disclaimer, the term of this patent is extended or adjusted under 35 U.S.C. 154(b) by 14 days.

(21) Appl. No.: 11/519,539

(22) Filed: Sep. 12, 2006

(51) Int. Cl.
*A01H 5/00* (2006.01)

(52) U.S. Cl. ..... Plt./224

(58) Field of Classification Search ..... Plt./224
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Acer palmatum,* 'Ryusen', characterized by a an unique true weeping plant habit, its rich fall color of red and gold coloration, and its ability to be readily grafted on *Acer palmatum* rootstock.

2 Drawing Sheets

Botanical classification: *Acer palmatum.*
Variety denomination: 'Ryusen'.

BACKGROUND OF THE INVENTION

The present invention relates to a new and distinct cultivar of *Acer palmatum,* and will be referred to hereafter by its cultivar name, 'Ryusen'. 'Ryusen' is a deciduous tree grown for use as a landscape plant.

The new *Acer* was discovered in Kawaguchi City, Saitama, Japan as a naturally occurring whole plant mutant in a maple nursery in summer of 1990. The parent plants of the new *Acer* are unknown.

'Ryusen' is selected as unique for its true weeping habit. 'Ryusen' is grafted onto root-stock of *Acer palmatum* and then trained as an upright plant until a desirable height before allowing the plant to naturally weep. The branching emerge at about a 45° angle and then become pendant almost vertically. The species, *Acer palmatum,* has an upright habit. The closest comparison cultivar known to the inventor is *Acer palmatum,* 'Jiro Shidare' (not patented). 'Jiro Shidare' is similar to 'Ryusen' in having green foliage with a cascading habit, however the branches of 'Jiro Shidare' are initially upright and then cascade with an arching habit to form a tree with an open, rounded habit, the branches are not strictly pendant as they are for 'Ryusen'.

Asexual reproduction of the new cultivar was first accomplished by grafting of terminal stem cuttings at Kawaguchi City, Saitama, Japan, by the inventor in 1996. The characteristics of this cultivar have been determined to be stable and are reproduced true to type in successive generations.

SUMMARY OF THE INVENTION

The following traits have been repeatedly observed and represent the characteristics of a three year-old graft of the new cultivar as observed in an outdoor test plot for one year in Atlanta, Ga. These attributes in combination distinguish 'Ryusen' as a unique cultivar of *Acer palmatum.*

1. 'Ryusen' has a unique growth habit; the branching have a true weeping habit.

2. Foliage color of 'Ryusen' is green in the spring and summer and turns to rich tones of red and gold in autumn.
3. 'Ryusen' is readily grafted onto *Acer palmatum* root-stock.

BRIEF DESCRIPTION OF THE DRAWING

The accompanying colored photographs illustrate the overall appearance and distinct characteristics of the new *Acer palmatum* as grown in Atlanta, Ga.

The photograph in FIG. 1 was taken in July and illustrates the weeping plant habit and foliage coloration of 'Ryusen' in summer as a three year-old graft on root-stock of *Acer palmatum.*

Figure 1:
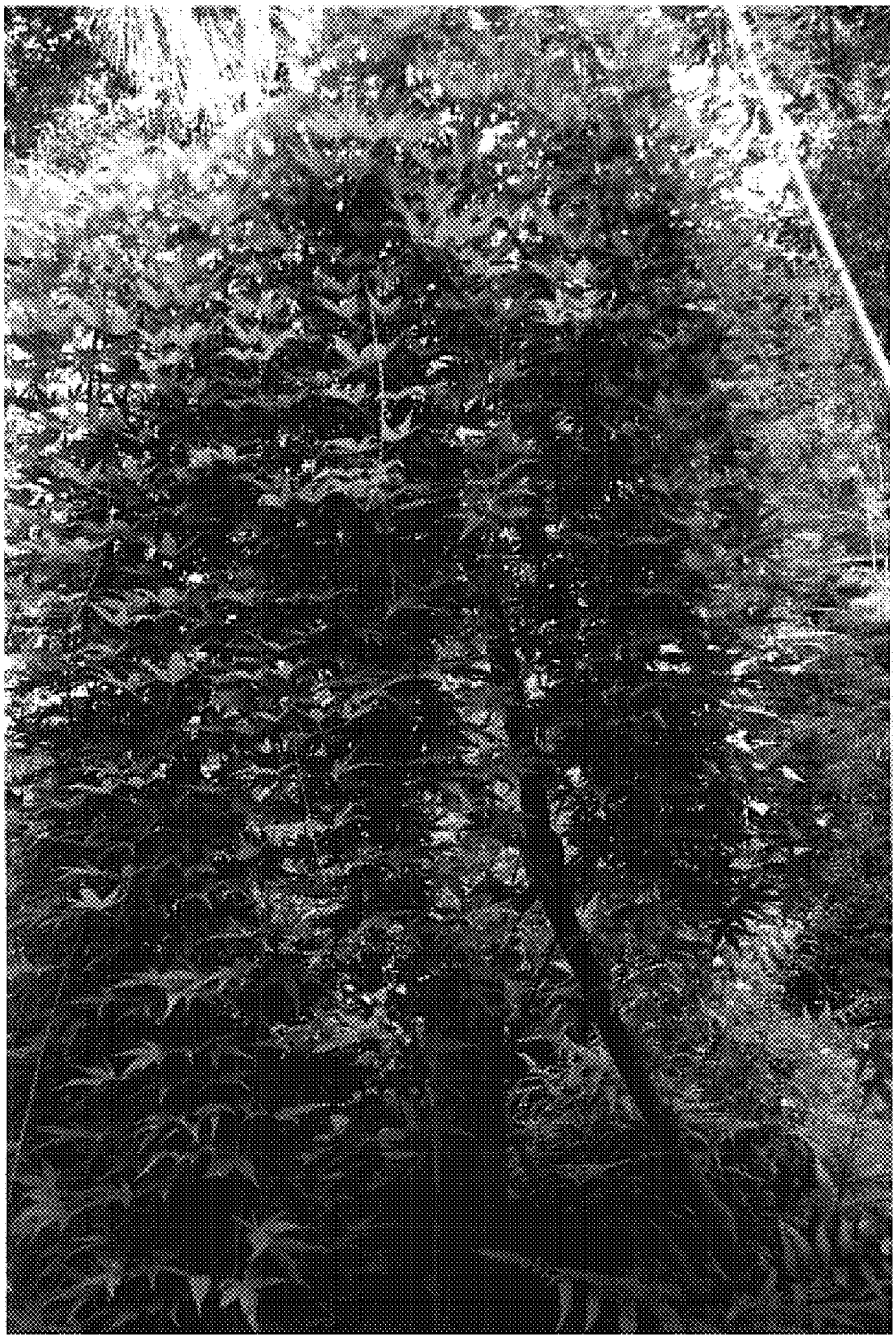
Figure 2:
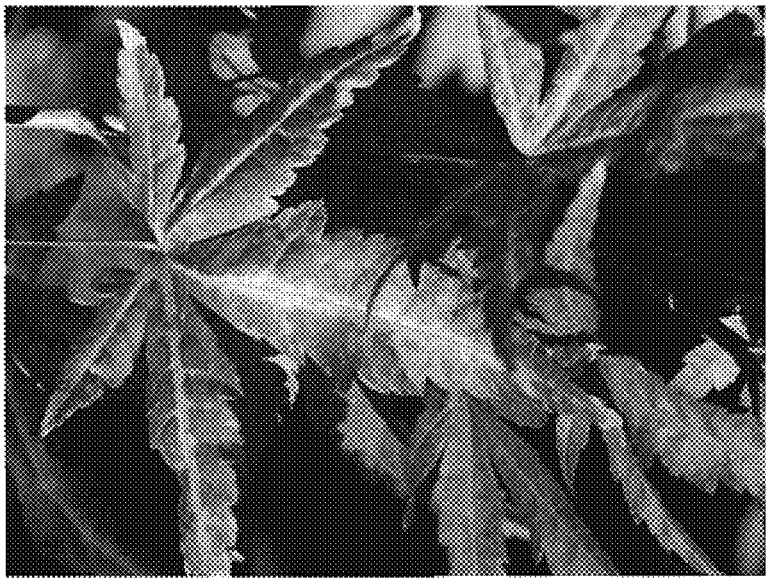
FIG. 2 and FIG. 3 are photographs that were taken in November and provide a view of the coloration of the fall foliage.
Figure 3:
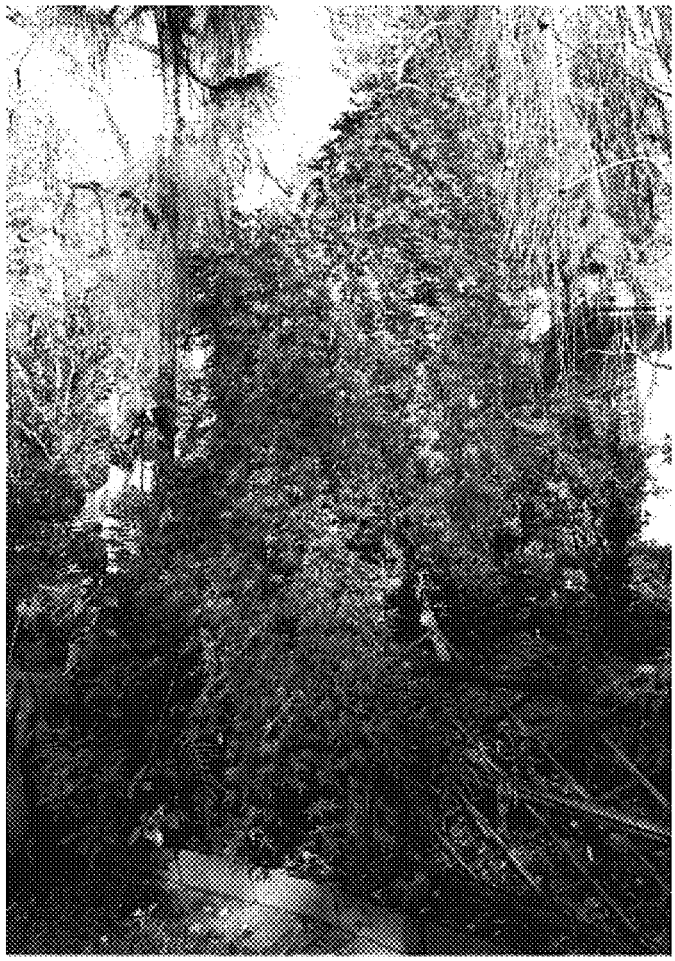

The colors in the photographs are as close as possible with the digital photography techniques available, the color values cited in the detailed botanical description accurately describe the colors of the new *Acer palmatum.*

DETAILED BOTANICAL DESCRIPTION

The following is a detailed description of a three-year old graft of the new cultivar as observed outdoors in partial shade in a trial garden in Atlanta, Ga. for one year. The phenotype of the new cultivar may vary with variations in environmental, climatic, and cultural conditions, as it has been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Ryusen' is a cultivar of *Acer palmatum.*

*Parentage.*—Naturally occurring whole plant mutation of *Acer palmatum.*

*Plant habit.*—Deciduous tree with pendant branches. 'Ryusen' is grafted onto root stock of *Acer palmatum* and then trained as an upright plant until a desirable height before allowing the plant to naturally weep. The branching emerge at about a 45° angle and then become pendant almost vertically.

*Height and spread.*—A three-year old plant grafted at about 1.8 m (6 ft), grows about 2.08 m (6.8 ft) if unstaked and growing naturally downward. The width with two grafts per root-stock is about 1 m (3 ft).

*Cold hardiness.*—U.S.D.A. Zones 5.

*Diseases and pests.*—No susceptibility or resistance to diseases or pests known to affect *Acer palmatum* has been observed for 'Ryusen'.

*Root description.*—Fibrous, freely branched.

Growth and propagation:

*Propagation.*—Grafted onto *Acer palmatum* root stock.

*Time required for graft development.*—About 4 weeks to develop in a 36-cell tree pot.

*Growth rate.*—Vigorous, growth rate of 0.5 to 1 m (1.5 to 3 ft) per growing season in Atlanta, Ga.

Stem description:

*Shape.*—Round.

*Stem color.*—Main stem 146A with striations of 165A, secondary branches 144A to 144B on lower surface and shaded branches, upper surface 176A (greyed-orange).

*Stem size.*—Main stems; up to 2.5 cm in diameter and about 2.5 m in length, lateral branches; up to about 50 cm in length and 4 mm in width on a six year-old graft.

*Stem surface.*—Glabrous.

*Internode length.*—About 2 to 4 cm on main branches, side branches typically 5 to 7 cm.

Foliage description:

*Leaf shape.*—Broadly ovate in overall outline, palmately five lobed.

*Leaf division.*—Simple.

*Leaf base.*—Hastate.

*Leaf apex.*—Acute.

*Leaf fragrance.*—None.

*Leaf venation.*—Palmate, 144C on upper surface and 144D on lower surface on summer foliage, 162B on both surfaces on fall foliage.

*Leaf margins.*—Palmate.

*Leaf arrangement.*—Opposite.

*Leaf aspect.*—Held upright on petioles held at about a 45° angle from branch.

*Leaf attachment.*—Petiolate.

*Leaf surface.*—Glabrous on upper and lower surface.

*Leaf size.*—Up to 9 cm in length and width, lobes; center lobe up to 6.5 cm in length and 2.5 cm in width, side lobes up to 5 cm in length and 1.8 cm in width, lower lobes up to 3.5 cm in length and 1.5 cm in width.

*Leaf color.*—Newly expanded and mature leaves in summer; upper surface 137A and lower surface 137B, fall foliage; Upper and lower surface 178B to 178C (greyed-red) with veins and some mottling of 162B (greyed-yellow), the greyed-yellow coloration is more prominent on the lower surface.

*Petioles.*—About 2 to 4 cm in length and 1 mm in width, held at about a 45° angle upward from branch, color is primarily 176A with areas of 145C at leaf attachment and branch attachment.

Inflorescence description:

*Inflorescence.*—Terminal Corymbs of small flowers, about 5 cm in width and 4.5 cm in depth.

*Flowers.*—Campanulate in shape, about 5 mm in length and 4 mm in depth, about 20 per corymb, not fragrant, 5-merous, N79B in color.

*Peduncle.*—Pedulant, about 4 cm in length and 1.5 mm in length, 145B to 145C in color.

*Pedicels.*—Average of 1.3 cm in length and 0.8 mm in width, 145C in color.

Reproductive organs: (Pistillate).

*Pistils.*—1, 2 stigmas, 145B to 145C in color, ovary superior.

*Fruit and seeds.*—Pair of 1-seeded winged samara, 145C to 145D in color when first formed and drying to 161D, about 1.8 cm in length and 6 mm in width, seeds are about 3.5 mm in diameter and N199B in color.

I claim:

1. A new and distinct cultivar of *Acer palmatum* plant named 'Ryusen' as herein illustrated and described.

* * * * *